US006960222B2

(12) United States Patent
Vo et al.

(10) Patent No.: US 6,960,222 B2
(45) Date of Patent: Nov. 1, 2005

(54) CATHETER HAVING A FUNNEL-SHAPED OCCLUSION BALLOON OF UNIFORM THICKNESS AND METHODS OF MANUFACTURE

(75) Inventors: Hung Van Vo, Sacramento, CA (US); Rainier Betelia, San Jose, CA (US)

(73) Assignee: Gore Enterprise Holdins, Inc., Newark, DE (US)

( * ) Notice: Subject to any disclaimer, the term of this patent is extended or adjusted under 35 U.S.C. 154(b) by 0 days.

(21) Appl. No.: 10/187,058

(22) Filed: Jun. 27, 2002

(65) Prior Publication Data

US 2003/0023204 A1 Jan. 30, 2003

Related U.S. Application Data

(63) Continuation-in-part of application No. 09/418,727, filed on Oct. 15, 1999, now Pat. No. 6,423,032, which is a continuation-in-part of application No. 09/333,074, filed on Jun. 14, 1999, now Pat. No. 6,206,868, which is a continuation-in-part of application No. PCT/US99/05469, filed on Mar. 12, 1999, which is a continuation-in-part of application No. 09/078,263, filed on May 13, 1998, now Pat. No. 6,413,235.

(30) Foreign Application Priority Data

Mar. 13, 1998 (AR) ........................................ P980101146

(51) Int. Cl.[7] .............................................. A61M 29/00
(52) U.S. Cl. ............... 606/200; 604/103.07; 604/96.01; 604/103.09
(58) Field of Search ................................ 606/191, 194, 606/195, 200; 604/96.01, 103.09, 97.03, 103.07, 99.01, 100.01, 101.02, 103, 103.1

(56) References Cited

U.S. PATENT DOCUMENTS

| 3,831,587 | A | * | 8/1974 | Boyd .......................... 600/207 |
| 4,571,240 | A | * | 2/1986 | Samson et al. .......... 604/103.1 |
| 4,575,371 | A | | 3/1986 | Nordqvist et al. |
| 4,781,681 | A | | 11/1988 | Sharrow et al. |
| 4,794,928 | A | | 1/1989 | Kletschka |
| 4,820,270 | A | | 4/1989 | Hardcattle et al. |
| 4,921,478 | A | | 5/1990 | Solano et al. |
| 5,074,845 | A | | 12/1991 | Miraki et al. |
| 5,102,415 | A | | 4/1992 | Guenther et al. |
| 5,171,305 | A | | 12/1992 | Schickling et al. |
| 5,441,485 | A | | 8/1995 | Peters |
| 5,601,581 | A | * | 2/1997 | Fogarty et al. ............. 606/159 |
| 5,833,650 | A | | 11/1998 | Imran |
| 5,997,503 | A | | 12/1999 | Willis et al. |
| 6,221,042 | B1 | | 4/2001 | Adams |
| 6,238,412 | B1 | | 5/2001 | Dubrul et al. |
| 6,264,631 | B1 | | 7/2001 | Willis et al. |
| 6,423,032 | B2 | | 7/2002 | Parodi |

* cited by examiner

*Primary Examiner*—Kevin C. Sirmons
(74) *Attorney, Agent, or Firm*—Kevin J. BoLand

(57) ABSTRACT

Methods and apparatus are provided for removing emboli during an angioplasty, stenting or surgical procedure comprising a catheter having a funnel-shaped occlusion balloon of uniform thickness disposed on a distal end of the catheter. The occlusion balloon is fused to the distal end so that it provides a substantially seamless flow transition into a working lumen of the catheter. Additionally, a distal edge of the occlusion balloon is configured to be in close proximity with an inner wall of a vessel to facilitate blood flow into the catheter and efficiently remove emboli.

24 Claims, 4 Drawing Sheets

CATHETER HAVING A FUNNEL-SHAPED OCCLUSION BALLOON OF UNIFORM THICKNESS AND METHODS OF MANUFACTURE

REFERENCE TO RELATED APPLICATIONS

The present application is a continuation-in-part of U.S. patent application Ser. No. 09/418,727, filed Oct. 15, 1999, now U.S. Pat. No. 6,423,032, which is a continuation-in-part of U.S. patent application Ser. No. 09/333,074, filed Jun. 14, 1999, now U.S. Pat. No. 6,206,868, which is a continuation-in-part of International Application PCT/US99/05469, filed Mar. 12, 1999, which is a continuation-in-part of U.S. patent application Ser. No. 09/078,263, filed May 13, 1998, now U.S. Pat. No. 6,413,235.

FIELD OF THE INVENTION

This invention relates to apparatus and methods for removing emboli during vascular interventions. More particularly, the apparatus and methods of the present invention provide a catheter having an occlusion balloon of uniform thickness that facilitates retrograde flow and removes emboli from a treatment vessel via a funnel-shaped taper of the occlusion balloon.

BACKGROUND OF THE INVENTION

Today there is a growing need to provide controlled access and vessel management during such procedures as stenting, atherectomy and angioplasty. Generally during these procedures there is a high opportunity for the release of embolic material. The emboli may travel downstream from the occlusion, lodging deep within the vascular bed and causing ischemia. The resulting ischemia may pose a serious threat to the health or life of a patient if the blockage forms in a critical area, such as the heart, lungs, or brain.

Several previously known apparatus and methods attempt to remove emboli formed during endovascular procedures by aspirating the emboli out of the vessel of interest using a catheter having an occlusion balloon. These previously known occlusion balloons, however, have various drawbacks, including variability in deployment of the balloon to the desired shape, inefficiency in removing emboli, and/or high cost and complicated processes associated with manufacturing the balloon.

In applicant's co-pending U.S. patent application Ser. No. 09/418,727, filed Oct. 15, 1999, which is incorporated herein by reference in its entirety, applicant describes the use of a bell or pear-shaped occlusion balloon disposed on the distal end of an arterial catheter. The occlusion balloon comprises a compliant material having a variable thickness along its length to provide a bell-shape when inflated. The balloon is affixed to distal end of the catheter so that a distal portion of the balloon extends beyond the distal end of the catheter to provide an atraumatic tip or bumper for the catheter.

The balloon of that catheter may be formed using previously known techniques, such as varying the thickness of the balloon wall to achieve the preferred bell-shape in the deployed position. Such processes, however, can lead to variability in the final product due to the manufacturing process. Because variable thickness balloons present greater difficulties during manufacture than balloons having uniform wall thickness, the cost of such balloons may be higher.

In view of the foregoing limitations of previously known devices, it would be desirable to provide an apparatus for removing emboli from a vessel comprising an occlusion balloon of uniform thickness to enhance manufacturability of the occlusion balloon.

It also would be desirable to provide an apparatus for removing emboli from a vessel comprising an occlusion balloon of uniform thickness to reduce manufacturing cost and enhance product yield.

It further would be desirable to provide an apparatus for removing emboli from a vessel comprising a catheter having an occlusion balloon of uniform thickness that facilitates retrograde flow and efficiently removes emboli.

SUMMARY OF THE INVENTION

In view of the foregoing, it is an object of this invention to provide an apparatus for removing emboli from a vessel comprising an occlusion balloon of uniform thickness to enhance manufacturability of the occlusion balloon.

It also is an object of the present invention to provide an apparatus for removing emboli from a vessel comprising an occlusion balloon of uniform thickness to reduce manufacturing cost and enhance product yield.

It further is an object of the present invention to provide an apparatus for removing emboli from a vessel comprising a catheter having an occlusion balloon of uniform thickness that facilitates retrograde flow and efficiently removes emboli.

The foregoing objects of the present invention are accomplished by providing interventional apparatus comprising a catheter having proximal and distal ends, a working lumen extending therethrough and an occlusion balloon having proximal and distal ends disposed on the distal end of the catheter. The occlusion balloon has a contracted state suitable for insertion into a vessel and a deployed state configured to occlude antegrade flow in the vessel.

In a preferred embodiment, the catheter comprises an inner layer covered with a layer of flat stainless steel wire braid and a polymer cover. A distal section of the occlusion balloon is melt-bonded to a distalmost end of the inner layer and, optionally, to a distalmost end of the polymer cover to form a substantially seamless transition into the working lumen of the catheter. The proximal end of the occlusion balloon is everted and affixed to the polymer cover to form an inflation chamber between the polymer cover and the balloon.

In the deployed state, the occlusion balloon is configured to extend distal of the catheter and provides a funnel-shaped transition into the working lumen of the catheter. A distal edge of the occlusion balloon is configured to be in close proximity with an inner wall of a vessel to facilitate retrograde flow into the working lumen of the catheter and efficiently remove emboli. Additionally, because the occlusion balloon of the present invention comprises a uniform thickness, the balloon may be more reliable, easier to manufacture and more cost-effective than an occlusion balloon having a variable thickness along its length.

Preferred methods of making and using the apparatus of the present invention also are disclosed.

BRIEF DESCRIPTION OF THE DRAWINGS

Further features of the invention, its nature and various advantages will be more apparent from the accompanying drawings and the following detailed description of the preferred embodiments, in which.

DESCRIPTION OF THE PREFERRED EMBODIMENTS

Figure 1A:
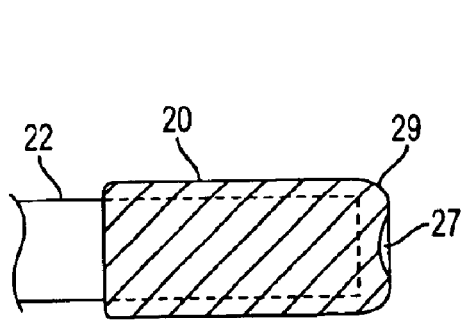
FIGS. 1A–1B are, respectively, side and sectional views of a previously known occlusion balloon in contracted and deployed states.
Figure 1B:
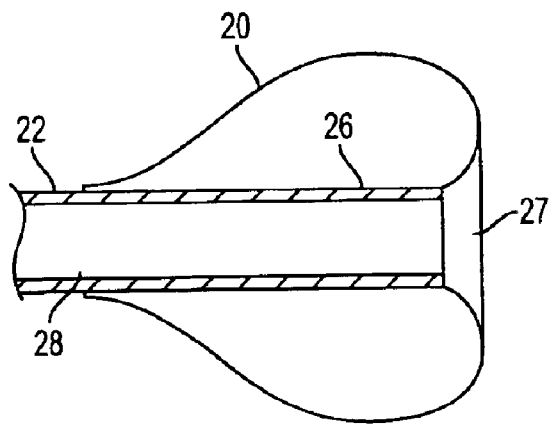

Referring to FIGS. 1A–1B, a bell-shaped occlusion balloon, as described in applicant's commonly assigned allowed U.S. patent application Ser. No. 09/418,727, filed May 8, 2001, which is incorporated herein by reference, is described. Occlusion balloon 20 is shown in contracted and deployed states in FIGS. 1A and 1B, respectively. Balloon 20 is affixed to distal end 26 of catheter 22, for example, by gluing or a melt-bond, so that opening 27 in balloon 20 leads into lumen 28 of catheter 22. Balloon 20 preferably is wrapped and heat treated during manufacture so that distal portion 29 of the balloon extends beyond the distal end of catheter 22 and provides an atraumatic tip or bumper for the catheter. In accordance with manufacturing techniques which are known in the art, occlusion balloon 20 comprises a compliant material, such as polyurethane, latex or polyisoprene which has variable thickness along its length to provide a bell-shape when inflated.

As described hereinabove, the variable thickness characteristic of occlusion balloon 20, which is used to deploy the balloon to the preferred bell-shape, presents certain manufacturing challenges. In particular, manufacturing a balloon having a variable wall thickness can lead to reduced yield due to variability of the manufacturing process. Additionally, a variable thickness balloon may be difficult to manufacture and may have a higher cost relative to a balloon having a uniform thickness.

Referring now to FIG. 2, a first embodiment of apparatus constructed in accordance with principles of the present invention is described. Apparatus 40 comprises catheter 41 having proximal and distal ends and working lumen 58 extending therethrough. Catheter 41 comprises occlusion balloon 42 having proximal and distal ends affixed to the distal end of catheter 41, and preferably comprises radiopaque marker band 65 disposed at the distal end of catheter 41 to facilitate positioning of the distal end of the catheter.

Occlusion balloon 42 comprises a uniform thickness material having a contracted state suitable for insertion into a vessel and a deployed state in which occlusion balloon 42 occludes antegrade flow in the vessel. In the deployed state, occlusion balloon 42 comprises distal taper 66 that is configured to provide a funnel-shaped transition into working lumen 58 so that blood flows in a non-turbulent fashion from a treated vessel into catheter 41. Additionally, distal edge 68 is configured to be in close proximity with an inner wall of a vessel to facilitate blood flow into catheter 41 and efficiently remove emboli.

Figure 2A:
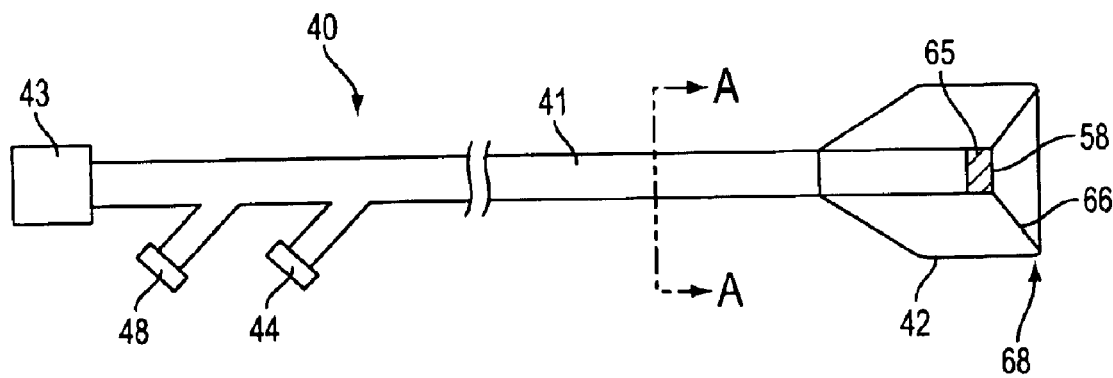
FIGS. 2A–2B are, respectively, a schematic view of apparatus in accordance with the present invention and a cross-sectional view along line A—A of FIG. 2A.
Figure 2B:
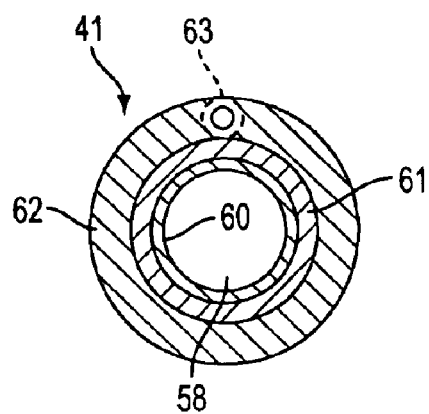

Catheter 41 preferably comprises inner layer 60 of low-friction polymeric material, such as polytetrafluoroethylene ("PTFE"), covered with a layer of flat stainless steel wire braid 61 and polymer cover 62 (e.g., polyurethane, polyethylene, or PEBAX), as shown in FIG. 2B. Working lumen 58 is defined as a lumen within an interior surface of inner layer 60. Inflation lumen 63 preferably is disposed within polymer cover 62 so that the inflation lumen does not substantially increase the overall profile of catheter 41.

Apparatus 40 preferably further includes proximal hemostatic port 43, e.g., a Touhy-Borst connector, inflation port 44, and blood outlet port 48. Inflation port 44 is coupled to inflation lumen 63, which in turn is coupled to occlusion balloon 42. Proximal hemostatic port 43 and working lumen 58 of catheter 41 are sized to permit interventional devices, such as angioplasty balloon catheters, atherectomy devices and stent delivery systems to be advanced through the working lumen when a guidewire (not shown) is positioned within the working lumen.

Blood outlet port 48, which is in fluid communication with working lumen 58, may be coupled to an external aspiration device, e.g., a syringe, to cause blood flow distal of occlusion balloon 42 to flow into working lumen 58. Alternatively, in a preferred embodiment, blood outlet port 48 may be coupled to a venous return catheter to form an arterial-venous shunt suitable for providing retrograde flow in a treatment vessel. This aspiration embodiment comprising an arterial-venous shunt is described in detail in applicant's commonly-assigned, above-incorporated U.S. patent application Ser. No. 09/418,727.

Figure 3A:
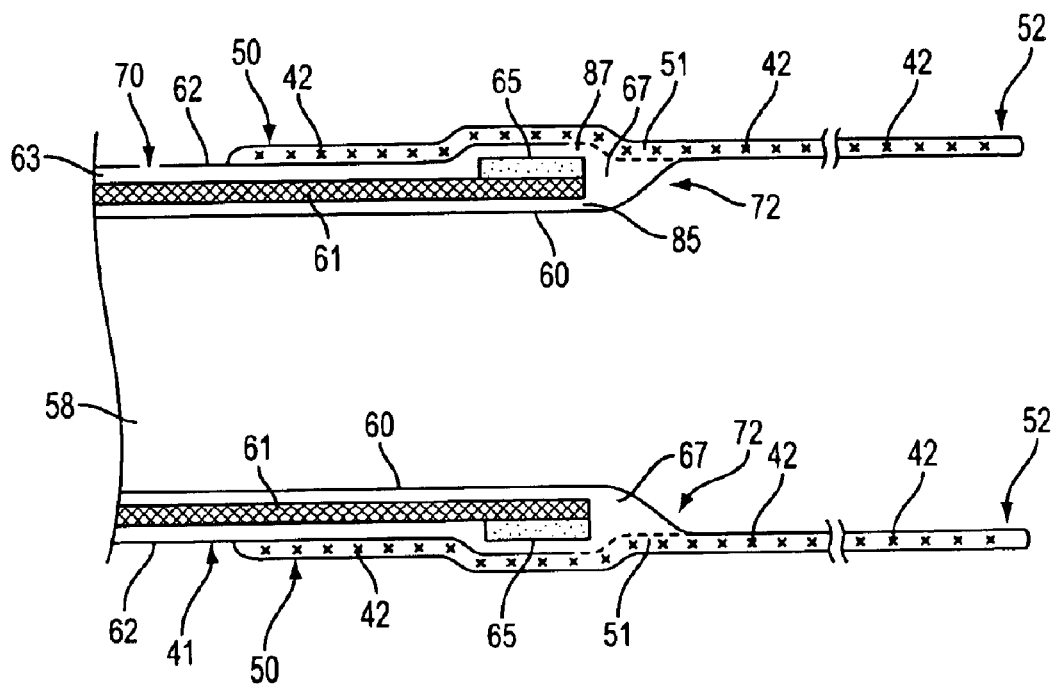
FIGS. 3A–3B are side sectional views illustrating a preferred configuration of the distal end of the catheter of FIG. 2.
Figure 3B:
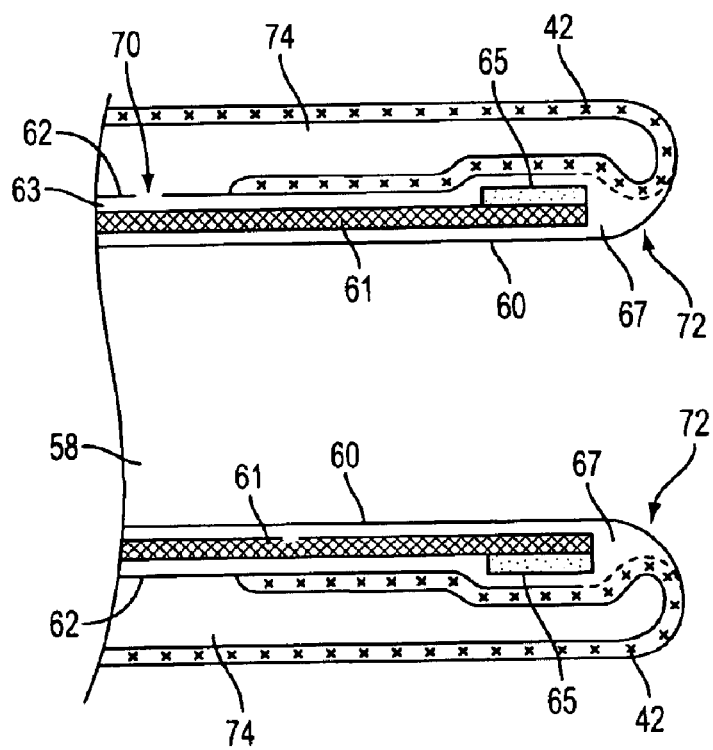

Referring now to FIG. 3, a preferred configuration of catheter 41 and a preferred method for affixing occlusion balloon 42 to the distal end of catheter 41 are described. In FIG. 3A, the distal end of catheter 41 is shown from a side sectional view as comprising inner layer 60 covered with a layer of flat stainless steel wire braid 61 and polymer cover 62. Radiopaque marker band 65 preferably is disposed at the distal end of catheter 41 between wire braid 61 and polymer cover 62, as shown in FIG. 3A. In accordance with principles of the present invention, occlusion balloon 42 comprises a uniform thickness along its length, as illustrated in FIGS. 3A–3B.

In a preferred method of manufacture, distal end 50 of occlusion balloon 42 is positioned atop polymer cover 62 near the distal end of catheter 41 and just distal of opening 70 of polymer cover 62, as shown in FIG. 3A. Distal end 50 of occlusion balloon 42 then is affixed to polymer cover 62, preferably using a melt-bond or, alternatively, using a biocompatible glue. At this time, proximal end 52 of occlusion balloon 42 extends freely beyond the distal end of catheter 41, as shown in FIG. 3A. For purposes of clarifying terminology used herein, although proximal end 52 of occlusion balloon 42 appears situated distal of distal end 50 in FIG. 3A, this is because proximal end 52 will subsequently be everted to extend proximal of distal end 50, as described hereinbelow.

In a next manufacturing step, distal section 51 of occlusion balloon 42, which is situated just proximal of distal end 50, is melt-bonded to at least one polymeric layer of catheter 41. Specifically, in a preferred embodiment, distal section 51 of occlusion balloon 42 is melt-bonded to distalmost end 85 of inner layer 60 and, optionally, to distalmost end 87 of polymer cover 62 to form fusion joint 67, as shown in FIG. 3A. The melt-bonding of the plurality of polymeric materials at fusion joint 67 provides substantially seamless transition 72 between occlusion balloon 42 and inner layer 60. Additionally, because fusion joint 67 is formed from a plurality of compliant polymeric materials, fusion joint 67 is capable of achieving a flexible range of motion.

Figure 4A:
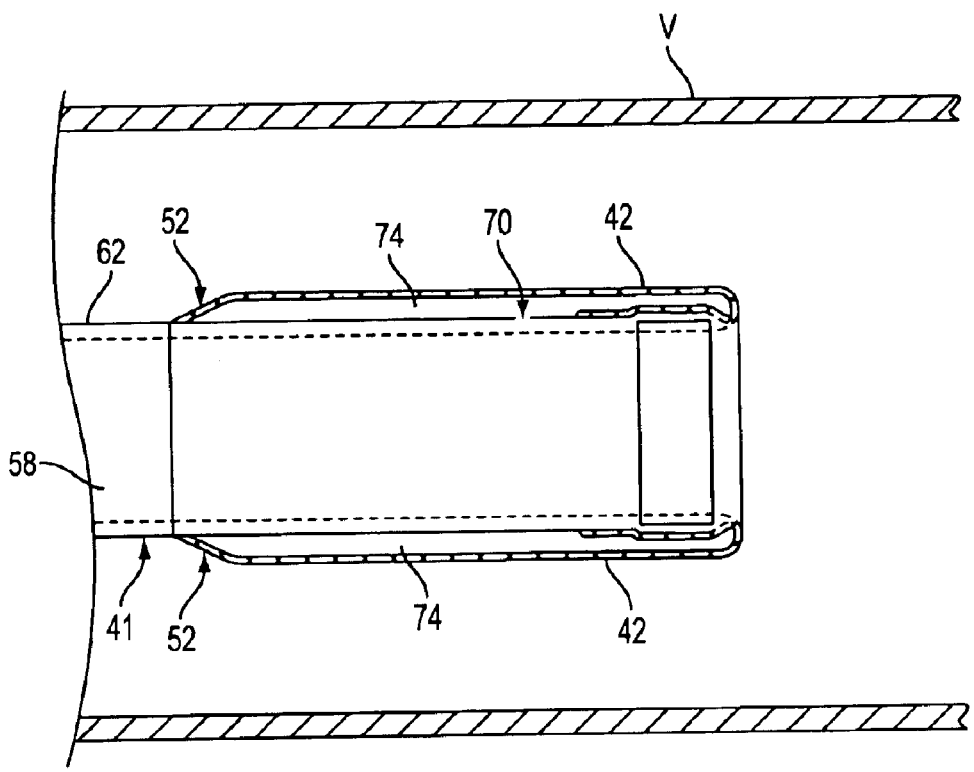
FIGS. 4A–4B are side sectional views of the occlusion balloon of the present invention in contracted and deployed states, respectively.

Proximal end 52 of occlusion balloon 42 then is everted so that it extends proximally and radially outward from catheter 41, as shown in FIGS. 3B and 4A. Proximal end 52 is affixed to polymer cover 62, preferably using a melt-bond or, alternatively, using a biocompatible glue, at a distance between about 10–20 mm proximal of the distal end of catheter 41, as shown in FIG. 4A. This creates inflation chamber 74 between polymer cover 62 and an interior surface of balloon 42. Opening 70, which is disposed in a lateral surface of polymer cover 62, is in fluid communication with inflation lumen 63 and inflation chamber 74, as shown in FIG. 3B. Proximal end 52 of occlusion balloon 42 may be stretched while it being affixed to polymer cover 62 so that apparatus 40 may achieve a reduced profile in the contracted state.

The fusion of occlusion balloon 42 to catheter 41 at fusion joint 67 and subsequent eversion of the balloon creates substantially seamless transition 72 into working lumen 58, as shown in FIG. 3B. In accordance with principles of the present invention, the provision of substantially seamless transition 72 may help reduce flow impedance into working lumen 58 and enhance flow within a treated vessel.

Figure 4B:
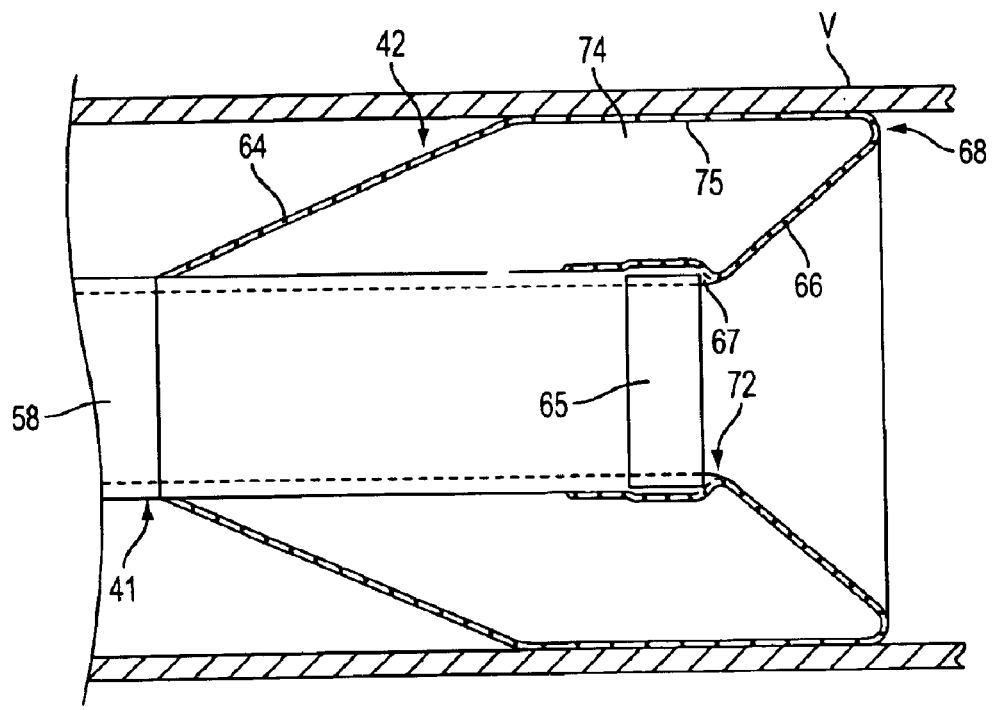

Referring now to FIGS. 4A–4B, deployment of apparatus 40 within vessel V of a patient is described. In FIG. 4A, occlusion balloon 42 is shown in a contracted state suitable for percutaneous and transluminal insertion into a patient's vessel. Occlusion balloon 42 is inflated via inflation port 44, inflation lumen 63 and opening 70, and deploys to a predetermined configuration having proximal taper 64 and distal taper 66, as shown in FIG. 4B. The predetermined configuration may be determined, for example, using a pre-molding process in accordance with manufacturing techniques that are known in the art. In the deployed state, an outer surface of central section 75, which is formed between proximal and distal tapers 64 and 66, is substantially flush with an inner wall of vessel V. As will be understood by those skilled in the art, the expanded diameter of central section 75 may be sized accordingly for different vessels.

Distal edge 68 is defined as a section of occlusion balloon 42 that is formed between central section 75 and distal taper 66. In the deployed state, distal edge 68 is configured to be in close proximity with an inner wall of vessel V to facilitate blood flow into working lumen 58 and efficiently remove emboli.

Distal taper 66 provides a funnel-shaped flow transition from distal edge 68 into working lumen 58. Additionally, as described hereinabove, fusion joint 67 provides substantially seamless transition 72 from occlusion balloon 42 into working lumen 58 due to the melt-bond between balloon 42 and inner layer 60 of catheter 41.

Figure 5:
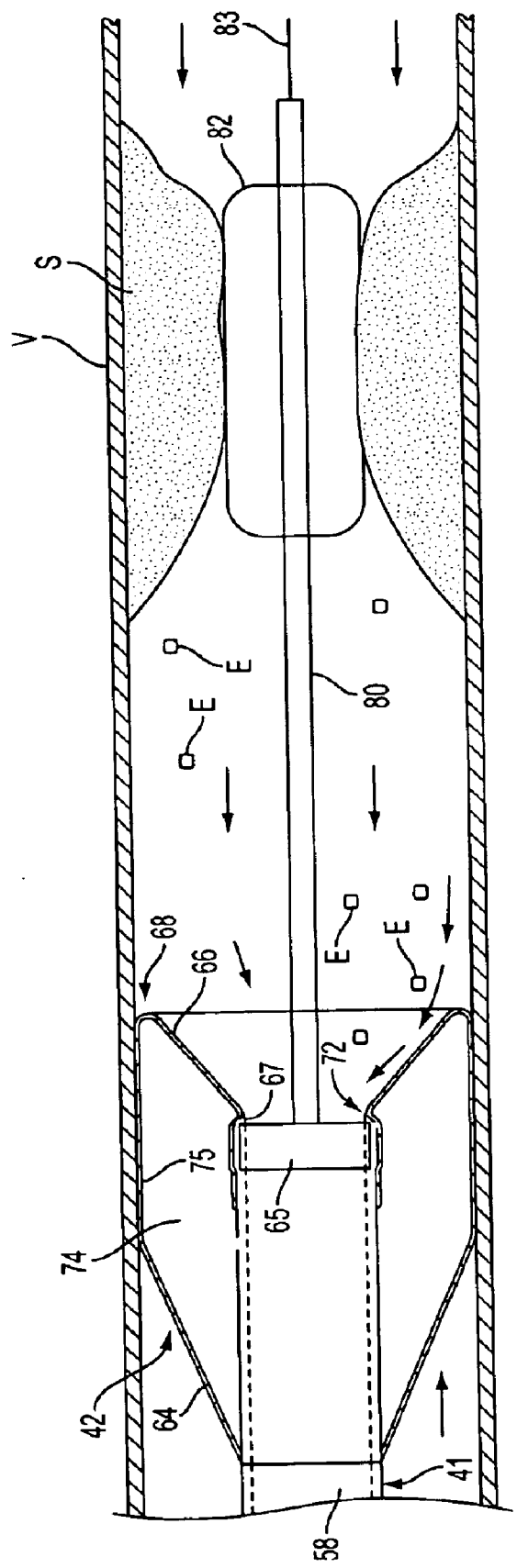
FIG. 5 is a schematic view of apparatus of the present invention being used during an interventional procedure.

Referring now to FIG. 5, a preferred method for using apparatus 40 of FIG. 2A during an interventional procedure, such as balloon angioplasty, is described. In a first step, guidewire 83 is inserted into a patient's vasculature and a distal end of guidewire 83 is disposed just proximal of stenosis S, which is located in vessel V. A dilator (not shown) that is disposed within catheter 41 then is inserted over guidewire 83 to advance catheter 41 to a desired position proximal of stenosis S. When catheter 41 is properly positioned, e.g., as determined under fluoroscopy using radiopaque marker band 65, the dilator may be removed. Occlusion balloon 42 then is inflated via inflation port 44 of FIG. 2A, preferably using a radiopaque contrast solution, to occlude antegrade flow in vessel V. Aspiration is provided through working lumen 58 of catheter 41 to cause retrograde flow to occur in vessel V distal of occlusion balloon 42, as illustrated by the arrows in FIG. 5.

Aspiration may be provided through working lumen 58 via blood outlet port 48 using an external aspiration device, e.g., a syringe, or alternatively using a venous return catheter to form an arterial-venous shunt, as described hereinabove.

An interventional instrument, such as conventional angioplasty balloon catheter 80 having balloon 82, may be loaded through hemostatic port 43 and working lumen 58 and positioned within stenosis S, preferably via guidewire 83. Hemostatic port 43 is closed and the angioplasty balloon is actuated to disrupt stenosis S. As seen in FIG. 5, emboli E formed during the interventional procedure are directed into working lumen 58 via the retrograde flow established.

Occlusion balloon 42 provides a substantially uniform funnel-shaped transition from an inner wall of vessel V into working lumen 58 of catheter 41. Distal edge 68, which is configured to be in close proximity with an inner wall of vessel V, facilitates flow into working lumen 58 and efficiently removes emboli. Additionally, the funnel-shaped transition provided by distal taper 66 and substantially seamless transition 72 into the working lumen via fusion joint 67 improves retrograde flow dynamics into working lumen 58.

Advantageously, because the present invention utilizes an occlusion balloon having a uniform thickness and relies on pre-molding of the occlusion balloon to obtain the desired deployed shape, a variable thickness occlusion balloon is not required. As noted hereinabove, use of an occlusion balloon having a uniform thickness provides several advantages, including enhanced manufacture, reduced cost and increased reliability.

While preferred illustrative embodiments of the invention are described above, it will be apparent to one skilled in the art that various changes and modifications may be made. The appended claims are intended to cover all such changes and modifications that fall within the true spirit and scope of the invention.

What is claimed is:

1. Apparatus for removing emboli from a vessel during an interventional procedure, the apparatus comprising:

a catheter having proximal and distal ends, a working lumen extending therethrough; to define an interior surface, and an exterior surface; and an occlusion balloon having a distal end affixed to the exterior surface of the catheter adjacent the distal end of the catheter and a proximal end everted to surround, and affixed to, the exterior surface of the catheter at a location proximal of the distal end of the catheter, the occlusion balloon having a contracted state suitable for insertion into a vessel and a deployed state configured to occlude antegrade flow in the vessel, the occlusion balloon having a substantially rhomboidal shape in the deployed state, wherein the occlusion balloon consists of a single sheet of elastomeric having a substantially uniform wall thickness, and in the deployed state, provides a funnel-shaped surface that extends beyond the distal end of the catheter, a portion of the distal end of the occlusion element also affixed to the interior surface of the catheter to provide a seamless transition into the working lumen.

2. The apparatus of claim 1 wherein the working lumen has an interior polymer cover.

3. The apparatus of claim 2 wherein the distal end of the occlusion balloon is fused to the interior polymer cover.

4. The apparatus of claim 3 wherein the distal end of the occlusion balloon is adhesively bonded to the interior polymer cover.

5. The apparatus of claim 1 wherein of the occlusion element is disposed in close proximity to the vessel wall in the deployed state.

6. The apparatus of claim 1 wherein an exterior surface of the catheter comprises an exterior polymer cover.

7. The apparatus of claim 6 wherein the proximal end of the occlusion balloon is fused to the exterior polymer cover.

8. The apparatus of claim 6 wherein the proximal end of the occlusion balloon is adhesively bonded to the exterior polymer cover.

9. The apparatus of claim 6 further comprising an inflation lumen disposed within the exterior polymer cover that is in fluid communication with the occlusion balloon.

10. The apparatus of claim 1 wherein the proximal end of the occlusion balloon is affixed to the exterior surface at a distance between about 10–20 mm proximal of the distal end of the catheter.

11. The apparatus of claim 1 further comprising a radiopaque marker band disposed at the distal end of the catheter.

12. The apparatus of claim 11 wherein the catheter comprises a wire braid disposed between the interior polymer cover and the exterior polymer cover, the apparatus further comprising a radiopaque marker band disposed between the wire braid and exterior polymer cover.

13. The apparatus of claim 1 further comprising a blood outlet port coupled to the proximal end of the catheter.

14. Apparatus for removing emboli from a vessel during an interventional procedure, the apparatus comprising:
- a catheter having proximal and distal ends, a working lumen extending therethrough, the catheter comprising an interior polymer cover defining the working lumen, an exterior polymer cover, and a wire braid disposed between the interior polymer cover and the exterior polymer cover;
- a radiopaque marker band disposed at the distal end of the catheter between the wire braid and the exterior polymer cover; and
- an occlusion balloon having a distal end affixed to the exterior polymer cover and a proximal end everted to surround, and affixed to the exterior polymer cover at a location proximal of the distal end of the catheter, the occlusion balloon having a contracted state suitable for insertion into a vessel and a deployed state configured to occlude antegrade flow in the vessel,
wherein the occlusion balloon comprises an elastomeric material having a substantially uniform wall thickness, and in the deployed state, provides a funnel-shaped surface, the distal end of the occlusion balloon also affixed to the interior polymer cover to form a seamless transition into the working lumen.

15. The apparatus of claim 14 wherein the distal end of the occlusion balloon is fused to the interior polymer cover.

16. The apparatus of claim 14 wherein the distalmost edge of the occlusion balloon is adhesively bonded to the interior polymer cover.

17. The apparatus of claim 14 wherein a distalmost edge of the occlusion element is disposed in close proximity to the vessel wall in the deployed state.

18. The apparatus of claim 17 wherein the distalmost edge of the occlusion element extends beyond the distal end of the catheter.

19. The apparatus of claim 14 wherein the proximal end of the occlusion balloon is fused to the exterior polymer cover.

20. The apparatus of claim 14 wherein the proximal end of the occlusion balloon is affixed to the exterior polymer cover at a distance between about 10–20 mm proximal of the distal end of the catheter.

21. The apparatus of claim 14 wherein the proximal end of the occlusion balloon is adhesively bonded to the exterior polymer cover.

22. The apparatus of claim 14 further comprising an inflation lumen disposed within the exterior polymer cover that is in fluid communication with the occlusion balloon.

23. The apparatus of claim 14 wherein the occlusion balloon further comprises a proximal taper and has a substantially rhomboidal shape in the deployed state.

24. The apparatus of claim 1 further comprising a blood outlet port coupled to the proximal end of the catheter.

* * * * *

UNITED STATES PATENT AND TRADEMARK OFFICE
CERTIFICATE OF CORRECTION

PATENT NO. : 6,960,222 B2
DATED : November 1, 2005
INVENTOR(S) : Vo et al.

It is certified that error appears in the above-identified patent and that said Letters Patent is hereby corrected as shown below:

Title page,
Item [73], Assignee, change "Holdins" to -- Holdings --.

Column 6,
Line 52, after "elastomeric" insert -- material --.
Line 66, after "wherein" insert -- a distalmost edge --.

Column 8,
Line 11, change "distalmost edge" to -- distal end --.

Signed and Sealed this

Seventh Day of March, 2006

JON W. DUDAS
*Director of the United States Patent and Trademark Office*